US006858730B2

(12) United States Patent
Ripperger

(10) Patent No.: US 6,858,730 B2
(45) Date of Patent: Feb. 22, 2005

(54) PROCESS FOR THE PRODUCTION OF HIGH PURITY MELAMINE FROM UREA

(75) Inventor: Willi Ripperger, Frankenthal (DE)

(73) Assignee: Casale Chemicals S.A. (CH)

( * ) Notice: Subject to any disclaimer, the term of this patent is extended or adjusted under 35 U.S.C. 154(b) by 0 days.

(21) Appl. No.: 10/380,305

(22) PCT Filed: Sep. 6, 2001

(86) PCT No.: PCT/EP01/10279

§ 371 (c)(1),
(2), (4) Date: Aug. 1, 2003

(87) PCT Pub. No.: WO02/22589

PCT Pub. Date: Mar. 21, 2002

(65) Prior Publication Data

US 2004/0010144 A1 Jan. 15, 2004

(30) Foreign Application Priority Data

Sep. 13, 2000 (EP) ............................................ 00119891

(51) Int. Cl.$^7$ ............................................ C07D 251/62
(52) U.S. Cl. ........................................ 544/203; 549/201
(58) Field of Search ................................ 544/201, 203

(56) References Cited

U.S. PATENT DOCUMENTS 5,514,796 A * 5/1996 Best et al. .................. 544/201
5,721,363 A   2/1998 Canzi et al.

FOREIGN PATENT DOCUMENTS

GB           1174848 A      12/1969

* cited by examiner

Primary Examiner—Peter O'Sullivan
(74) Attorney, Agent, or Firm—Akerman Senterfirt

(57) ABSTRACT

A method for purifying melamine comprising impurities like ureido-melamine, oxotriazines, melam, melem, comprises the step of putting into contact at a temperature comprised between 340° C. and 410° C. and at a pressure comprised between 8 and 17 MPa a melamine melt with a bed of a catalyst thus obtaininig melamine with a purity of at least 99%.

15 Claims, 2 Drawing Sheets

PROCESS FOR THE PRODUCTION OF HIGH PURITY MELAMINE FROM UREA

FIELD OF THE INVENTION

According to its general aspect the present invention relates to a high-pressure non-catalytic process for the production of high purity melamine from urea.

More in particular, the invention relates to a method for purifying melamine from impurities like ureido-melamine, oxotriazines, melam, melem and non-converted urea in the form of isocyamic acid by an appropriate physical-chemical treatment. The treatment is preferably but not exclusively carried out within the non-catalytic process, so as to obtain melamine with a purity of 99% and higher.

PRIOR ART

The modem processes of melamine synthesis can be classified into two categories: the catalytic low-pressure processes and the non-catalytic high-pressure processes. All processes are characterised by three process stages: a) syntheses; b) Melamine purification and recovery; c) the off-gas treatment. An overview of the prior art is given in (Ulmann's Encyclopaedia of Industrial Chemistry, Vol. A 16, p. 171–181(1990)).

In a high-pressure non-catalytic process a urea melt from the off-gas scrubber is fed to the high-pressure reactor, operated at a pressure between 6 and 15 Mpa and in the temperature range of 390–410° C. The urea is pyrolised to melamine according to the equation

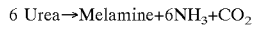

$$6\ \text{Urea} \rightarrow \text{Melamine} + 6NH_3 + CO_2$$

To enhance the reaction and to suppress the formation of by-products, additional ammonia is fed to the reactor in an amount of 0.2–1.0 Kg ammonia/Kg urea and the residence time in the reactor, referring to the urea feed, is between 0.5–2 hours. The reaction products in the reactor consist of molten melamine comprising by-products like ureido-melamine, oxotrizines, melam, melem and non-converted urea in the form of Isocyamic Acid. The Melamine melt is transferred under pressure, together with $CO_2$ and $NH_3$ as a mixed stream, to a gas-liqid separator. In the gas liquid separator which is kept at virtually the same pressure and temperature at the reactor vessel, the reaction gases are separated from the melamine melt.

The gaseous stream, which contains the reaction gases ammonia and carbon-dioxide, the added ammonia, non-converted isocyamic acid and also melamine vapour, is sent to the urea scrubber where it is scrubbed at virtually the same pressure, with molten urea so as to preheat the urea, cool said off-gases and remove the melamine from the off-gases. Isocyanic acid is reconverted to urea in the scrubber. The preheated urea, which contains the removed melamine is sent to the reactor.

The liquid melamine melt from the gas-separators, which contains still the above mentioned impurities, ureido-melamine, oxotriazines, melam, melem as well as uncon-verted isocyamic acid besides dissolved ammonia and carbon-dioxide can not be simply cooled to solid melamine. This melamine would contain too much impurities and could not be used for technical purposes. Normally, customary melamine has a purity >99.5% more preferably >99.8%. To produce such a high-purity melamine, the melamine melt is either: quenched with an aqueous ammonia solution, dissolved, filtered and re-crystallised or molten melamine is vaporised by a stream of ammonia from the melt or trans-ferred to a so called ageing-unit where the melt or the already solid melamine is treated by increasing the ammonia pressure at higher temperature and longer residence times.

A water quench for removing and reducing the impurities is used for example, by the Nissan process ("Technical development of melamine Manufactured by Urea process" by A. Shiroishi et al., Chemical economy & Engineering review, vol. 8, 1976, page 35 ff.), the Montedison process ("The manufacture of Non-fertiliser Nitrogen Products" Nitrogen No. 139, p 32–39, (1982)) and lately by the Eurotecnica process ("A Challenging Opportunity", Nitro-gen & Methanol, No. 233, page 35–40, (1998)).

In principle, in all three processes the mixture of melamine melt and the off-gases coming from the reactor are separated or not into a gaseous stream and a liquid stream, consisting mainly of melted melamine. The liquid stream is quenched with an aqueous ammonia solution, in which the melamine is dissolved. The solution is maintained for a definite period of time at higher temperature and pressure, during which the impurities are said to be eliminated.

Thereafter follows a further treatment with numerous apparatus, including filtration, crystallisation and a costly waste water treatment section. The number of unit opera-tions in a melamine plant with such quenching units is very high which rises the investment costs as well as the oper-ating cost considerably. This is a serious drawback of such plants.

To avoid this costly units for quenching with an aqueous ammonia solution and following purification by crystallisation, a purification by evaporation of the melamine melt has been proposed (WO 95/01345, WO 97/34879). After separation of the off-gases from the melamine melt, the liquid melamine melt is directed to a vaporiser and is vaporised therein by lowering the pressure and/or feeding ammonia gas into the vaporiser. The melamine containing ammonia gas obtained from the vapor-iser is cooled in a quencher, preferably with ammonia gas. Though the melamine obtained has a sufficient purity, this process has the disadvantage of a high energy consumption:

To evaporate the melamine from the melt, the heat of vaporisation must be raised which cannot, or only at a very low temperature level, be recovered.

To enhance the evaporation of the melamine, a minimum of 2.4 Kg, ammonia per Kg of melamine is needed to vaporise the melamine. So, large amounts of gas are to be handled.

To avoid the above mentioned drawbacks of the different processes Melamine chemicals, U.S. Pat. No. 4,565,867, has developed a very simple high pressure process in which the quantity of apparatus is quite small as compared with the Montedison, Nissan or Eurotecnica process. However, the purity of the melamine obtained is only 95–97.5% in a commercial plant.

To combine the advantage of a simple high-pressure process like the Melamine Chemicals process, with a high product quality numerous proposals had been made.

One method described (WO 98/04533, WO 98/52928, WO 98/55465, WO 98/55466, WO 98/20183, WO 96/20183, WO 98/23778, WO 00/21940, U.S. Pat. No. 5,514,797) is the after treatment of the already solidified melamine powder or crystals under high ammonia pressure and at elevated temperature. Pressure up to 50 Mpa and temperatures between 270–354° C. are claimed for the after treatment. A noticeable reduction of the melam and melem content is only achieved at ammonia pressures above 7.5 MPA, as shown in the examples. Furthermore, because this reaction takes place in the solid state, long residence time, up to 5 hours, and mechanical agitation are necessary. For all the persons skilled in the art, these restrictions are serious disadvantages.

As an alternative to the treatment of solid melamine the after-treatment of the melamine melt under high ammonia pressure and higher temperatures is described (WO 96723778, WO 96/20182, EP 0808 836 A1). The liquid, melamine melt, separated from the reaction gases ammonia and carbon-dioxide, is subjected to a treatment with ammonia at temperature between 430° C. and the melamine melting point under an ammonia partial pressure from 5 to 40 MPa during a mean resting time up to 8 hours. After that the melamine melt is cooled down with a controlling rate to a temperature from 320° C. to 270° C. and then expanded and cooled down to room temperature.

All these methods have the disadvantage that the pressure level within the plant has to be increased considerably above the reaction pressure of the reactor and gas purification unit and longer residence times of the melt are necessary to achieve a sufficient reduction of the by-product content This is a serious handicap for a continuos process operation, apart from the cost for the compression of the ammonia gas.

On the other side the multitude of published patents show the importance of getting melamine of high purity from the high-pressure, non-catalytic processes.

SUMMARY OF THE INVENTION

The technical problem underlying the present invention is to provide a method for obtaining melamine at high purity in a simple and reliable manner, without the drawbacks of the prior art The problem is solved by a method for purifying melamine from impurities like ureido-melamine, oxotriazines, melam and melem, characterized in that a melamine melt is put into contact at a temperature comprised between 340° C. and 410° C. and at a pressure comprised between 8 and 17 MPa with a bed of a catalyst thus obtaining melamine with a purity of at least 99%.

Preferably, the catalyst is selected from the group comprising alumina, silica, alumina/silica, molecular sieves, mixtures and derivatives thereof.

According to a preferred embodiment of the invention, the catalyst also has adsorptive properties.

Preferably said melamine containing impurities is obtained from urea by a high-pressure non-catalytic process.

Advantageously said melamine containing impurities in the melt state is fed with a continuous flow to a purification unit comprising one bed of said catalyst.

Preferably, said continuous flow of melamine melt is fed to the purification unit with a flow rate comprised between 0.5 and 10 Kg of melamine melt/(litre catalyst×hour), for instance between 1 and 10 Kg of melamine melt/(litre catalyst×hour)

Preferably, the contact between the melamine melt with the bed of the catalyst is carried out in the presence of $NH_3$. Preferably, said $NH_3$ is dissolved in said melamine.

According to the research work carried out by the Applicant, the surprising results obtained with the above purification method could be explained by the catalyst who promotes the reaction of impurities such as ureidomelamine, oxotriazines, ammeline, ammelide, cyanuric acid, melam, melem and melon to melamine. Improved results have further been obtained by the use of a catalyst with additional adsorptive properties: non-converted higher molecular compounds such as melam, melem and melon are thus removed from the melamine melt by adsorption.

According to a further embodiment, the present invention relates to a method for purifying melamine comprising impurities like melam, melem, melon, characterized in that a melamine melt is put into contact at a temperature comprised between 340° C. and 410° C. and at a pressure comprised between 8 and 17 MPa with a bed of an adsorbent material.

Preferably, the adsorbent material is selected from the group comprising alumina, silica, alumina/silica, active carbon, natural clays, molecular sieves, mixtures and derivatives thereof.

Among the many advantages obtained with the present invention it is worth citing that a melamine conversion yield up to 99.9% may be achieved.

Moreover, operating pressure and temperature of the present method can be substantially equal to those used in the non-catalytic melamine synthesis process from urea, so that no changes are required in the operating conditions during the production process.

It is also advantageously possible to carry out the melamine purification directly and in continuous within the same plant for the non-catalytic production of high purity melamine from urea.

DETAILED DESCRIPTION OF THE DRAWINGS

Figure 1:
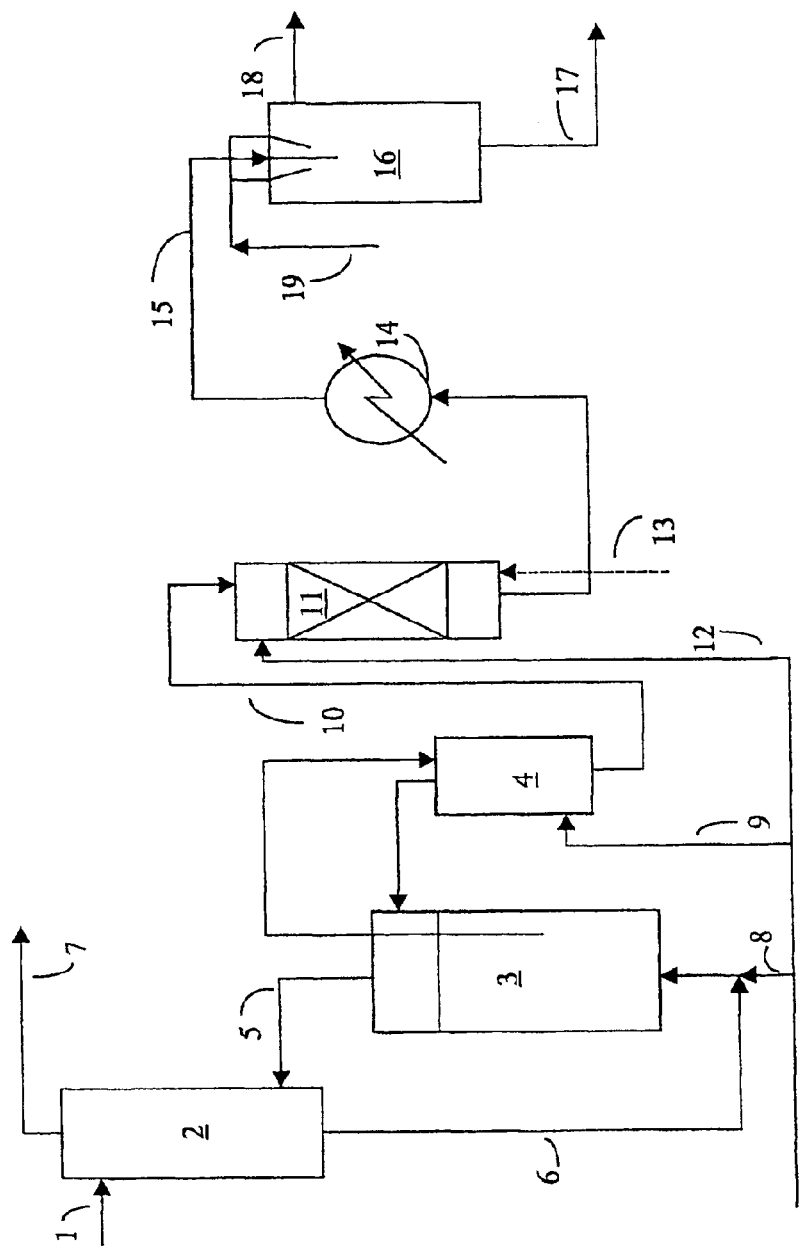
FIG. 1 shows a flow diagram of a melamine plant according to the present invention.

With specific reference to FIG. 1 is a detailed description of a preferred embodiment of the present invention.

It is shown a flow diagram of a complete plant-system for the manufacture of melamine from urea in a high-pressure process and shows how the invention can be integrated into an existing plant or in a new one.

Liquid urea is fed to a gas scrubber (2) via line (1). Via line (5), a gas stream consisting mainly of $NH_3$, $CO_2$ and gaseous melamine is transferred from the melamine reactor (3), which is connected directly with the gas-liquid separator (4) to the gas scrubber (2). In the gas-scrubber (2) the melamine is scrubbed from the gas stream by means of the urea supplied via line (1). Via line (6) the liquid urea with the melamine and dissolved $NH_3$ and $CO_2$ enters through a nozzle the melamine reactor (3). Via line (8) additional $NH_3$ can be fed to the melamine reactor.

A gas stream consisting of $NH_3$ and $CO_2$ leaves the gas scrubber (2) via line (7) to an adjoining urea plant. In the reaction vessel (3) the urea is reacted at 390° C.–410° C. and 8–17 MPa to $NH_3$, $CO_2$ and melamine. The liquid melamine is separated from the reaction gases on the top of the melamine reactor (3) and in the connected gas-separator (4). To strip off the last traces of $CO_2$ from the melamine melt, pressurised $NH_3$ is fed via line (9) to the gas separator (4).

The liquid melamine melt from the gas-separator (4), which is practically free of $CO_2$ and saturated with NH3, is directed via line (10) to the purification unit (11) according to this invention. In this unit a catalyst removes the impurities by catalytic conversion and—depending on the catalyst used—also by adsorption. The purification unit (11) has practically the pressure as the melamine reactor (3) and gas-separator (4). The temperature of the purification unit

(11) can be adjusted to the amount of impurities, preferably the temperature is between 360 and 410° C. In other words, the pressure and the temperature in unit (11) can be substantially the same as in the melamine reactor (3). It is also possible that lower pressure and/or temperature are used in unit (11).

To enhance the catalytic conversion of the impurities additional ammonia can be fed to the purification unit via line (12). Via dashed line (13) low pressure steam, when necessary, can be introduced into the purification unit to regenerate the catalyst.

In the subsequent product cooler (14) the melamine melt, saturated with ammonia, is cooled slightly above its melting point under the reaction conditions. In another embodiment of the invention the product cooler (14) is installed directly after the gas-separator (4) and before the purification unit (11).

After passing the product cooler (14) the melamine melt is sent via line (15) to the quenching section (16), where the melamine melt is depressurised and cooled with liquid ammonia, added by line (19). The resulting solid melamine powder is discharged via line (17), the gaseous ammonia is discharged via line (18), liquefied and recycled to the quenching section (16).

Figure 2:
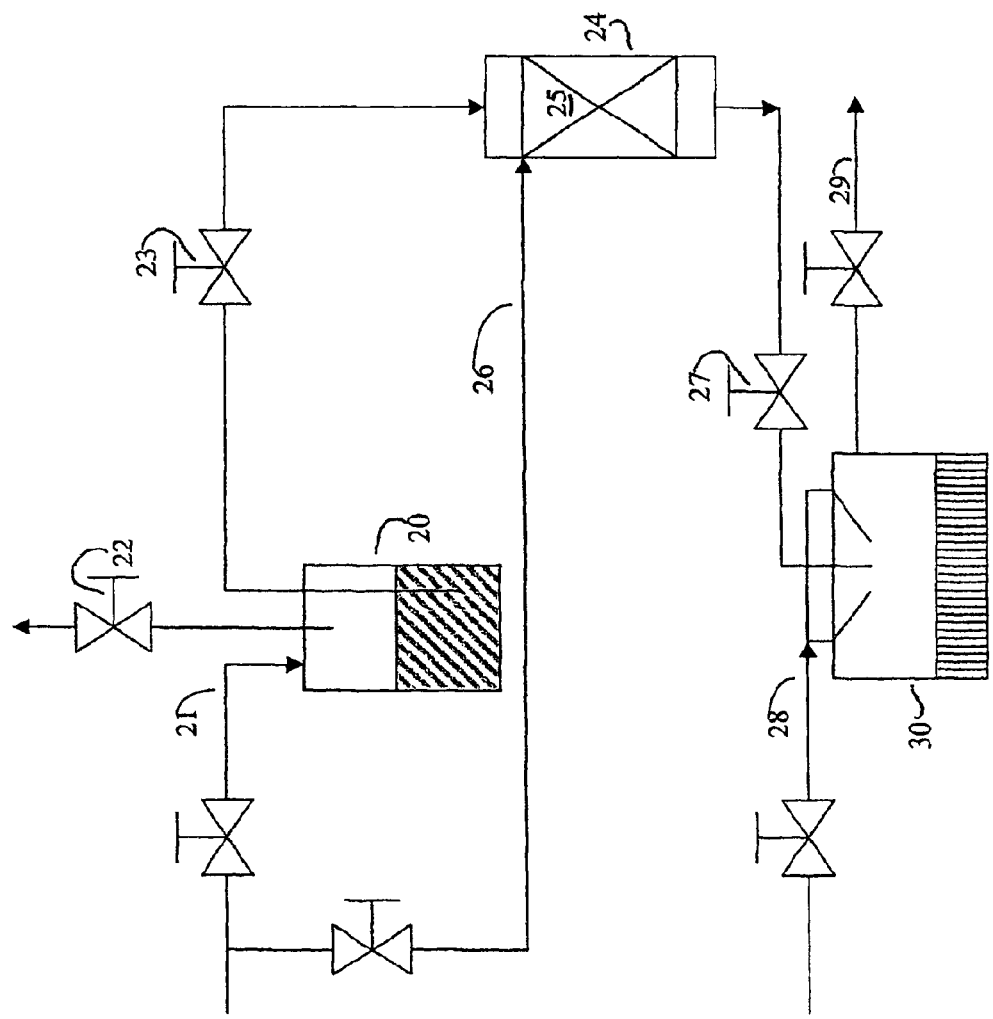
FIG. 2 shows a test apparatus to detect melamine purity.

With specific reference to FIG. 2, it is shown a test apparatus wherein the effectiveness of the invention was demonstrated.

Solid melamine is filled in the autoclave (20). Then the autoclave is pressurised with $NH_3$ via line (21) to the desired pressure and heated to the desired temperature, normally in the range of 360°–410° C. During the heating up period the pressure increases, surplus $NH_3$ is released by valve (22). After reaching the desired temperature and pressure and all the melamine is melted, valve (23) is opened and the melamine melt is fed to the purification unit (24), which is filled with the catalyst (25). Line (26) indicates a $NH_3$ feed to the purification unit (24).

After passing the catalyst (25), the melamine melt is expanded via valve (27) into the quencher (30). In the quencher the melamine melt is effectively cooled by liquid ammonia fed via line (28) below 250° C. The pressure in the quencher (30) is appropriately adjusted to the pressure in the purification unit. Evaporated ammonia is released by the valve (29).

At the end of the test, the accumulated melamine is taken from the quencher and analysed by High Pressure Liquid Chromatography (HPLC). The following examples demonstrate the effectiveness of the invention.

EXAMPLE 1

Melamine with the following composition (wt %):

| | |
|---|---|
| Melamine | 97.5 |
| Melam | 1.91 |
| Melem | 0.14 |
| Ureido-Melamine | 0.05 |
| Oxotriazines | 0.4 | was melted in the autoclave and the melamine melt passed at different flow rates over a catalyst in the purification unit according to FIG. 2 under the following conditions:

| | |
|---|---|
| Catalyst Volume (ml) | 500 |
| Catalyst Type | $Al_2O_3$ (activated alumina) |
| Temperature (° C.) | 400 |
| Pressure (MPa) | 15 |
| $NH_3$ added (wt % of melamine) | 5 |

The "flow rate" is defined as the hourly melamine feed in Kg per volume of catalyst, given in litres. In several test runs the following results have been received (mean values)

| Flow rate | 4 | 7 |
|---|---|---|
| Product Composition (wt %) | | |
| Melamine | 99.9% | 99.6% |
| Melam | — | — |
| Melem | <0.01 | <0.01 |
| Ureido-Melamine | — | — |
| Oxotriazines | — | — |

"—" means not detectable by HPLC

EXAMPLE 2

| Melamine with the following composition (wt %) | |
|---|---|
| Melamine | 95.3 |
| Melam | 1.30 |
| Melem | 0.74 |
| Ureido-Melamine | 1.53 |
| Oxotriazines | 0.90 |

Was melted and treated in the purification unit as described in example 1 under the following reaction conditions:

| | |
|---|---|
| Catalyst Volume (ml) | 500 |
| Catalyst Type | $Al_2O_3/SiO_3$ (Silica/alumina) |
| Temperature (° C.) | 400 |
| Pressure (MPa) | 8 |
| $NH_3$ added (wt % of melamine feed) | 5 |

The following results had been received depending on the flow rate:

| Flow rate | 2 | 4 |
|---|---|---|
| Product Composition (wt %) | | |
| Melamine | 99.6% | 99.3% |
| Melam | 0.1 | 0.4 |
| Melem | <0.01 | <0.01 |
| Ureido-Melamine | — | — |
| Oxotriazines | — | 0.01 |

EXAMPLE 3

The example shows the possibility to remove melam and melem from a liquid melamine melt essentially by adsorption. Melamine with 1000 ppm melem and 1500 ppm melam was molten and fed to the purification unit as described above under the following conditions:

| | |
|---|---|
| Adsorbent Volume (ml) | 500 |
| Adsorbent Type | Al$_2$O$_3$ ($\gamma$ Alumina) |
| Temperature (° C.) | 360 |
| Pressure (MPa) | 15 |
| Flow rate | 4 Kg Melamine/l adsorbent × h |

Under these conditions the melem content was reduced to 40–80 ppm, the content of melam in the product was reduced to 350–500 ppm.

As it is apparent to one skilled of the art various modifications are possible within the scope of this invention. For example, the invention can be applied to all existing high-pressure process with quite different compositions of the melamine melt coming from the synthesis section of a high pressure process.

In particular, the purifying unit (11) can be installed later into an existing melamine plant. There is a high flexibility concerning pressure, temperature and amount and type of impurities to be removed, on the one hand by the selection of suitable catalysts and or adsorbent materials, on the other hand by varying the dimension of the reactor and/or the flow rate.

Furthermore, it is possible to operate various modifications on said catalysts and or adsorbent materials, e.g. surface area, pore volume, pore diameter, acid properties etc.

What is claimed is:

1. Method for purifying melamine comprising impurities characterized in that a melamine melt is put into contact at a temperature comprised between 340° C. and 410° C. and at a pressure comprised between 8 and 17 MPa with a bed of a catalyst thus obtaining melamine with a purity of at least 99%.

2. Method according to claim 1, characterized in that said catalyst is selected from the group comprising alumina, silica, alumina/silica, molecular sieves, mixtures and derivatives thereof.

3. Method according to claim 1, characterized in that said catalyst adsorptive properties.

4. Method according to claim 1, characterized in that said melamine containing impurities is obtained from urea by a high-pressure non-catalytic process.

5. Method according to claim 1, characterized in that the contact between said melamine melt with the bed of catalyst is carried out in the presence of NH$_3$.

6. Method according to claim 5, characterized in that said NH$_3$ is dissolved in said melamine.

7. Method according to claim 1, characterized in that said melamine melt is fed with a continuous flow to a purification unit comprising at least one bed of said catalyst.

8. Method according to claim 7, characterized in said continuous flow of melamine melt is fed to said purification unit with a flow rate comprised between 0.5 and 10 Kg of melamine melt/(litre catalyst×hour).

9. Method according to claim 7, characterized in that said melamine melt is obtained from a high-pressure non-catalytic process and directly fed to said purification unit.

10. Method for purifying melamine comprising impurities characterized in that a melamine melt is put into contact at a temperature comprised between 340° C. and 410° C. and at a pressure comprised between 8 and 17 MPa with a bed of an adsorbent material.

11. Method according to claim 10, characterized in that said adsorbent material is selected from the group comprising alumina silica, alumina/silica, active carbon, natural clays, molecular sieves, mixtures and derivatives thereof.

12. High-pressure non-catalytic process for the production of a melamine from urea characterized by, in a purification step, putting a melamine melt into contact at a temperature comprised between 340° C. and 410° C. and at a pressure comprised between 8 and 17 MPa with a catalyst or an adsorbent material thus obtaining melamine with high purity.

13. Method according to claim 8, characterized in said continuous flow of melamine melt is fed to said purification unit with a flow rate comprised between 1 and 10 Kg of melamine melt/(liter catalyst×hour).

14. Method according to claim 10 characterized in that the impurities are one or more of melam, melem or melon.

15. Method according to claim 1 characterized in that the impurities are one or more of ureido-melamine, oxotriazines, melam or melem.

* * * * *